United States Patent
Holm et al.

(10) Patent No.: US 7,927,848 B2
(45) Date of Patent: Apr. 19, 2011

(54) METHOD AND APPARATUS FOR PRODUCTION OF BIOGAS FROM AN ORGANIC MATERIAL

(75) Inventors: Stig Holm, Linköping (SE); Jörgen Ejlertsson, Rimforsa (SE); Bertil Carlson, Linköping (SE)

(73) Assignee: Tekniska Verken I Linkoping AB, Linkoping (SE)

( * ) Notice: Subject to any disclaimer, the term of this patent is extended or adjusted under 35 U.S.C. 154(b) by 1219 days.

(21) Appl. No.: 10/524,190

(22) PCT Filed: Jul. 7, 2003

(86) PCT No.: PCT/SE03/01177
§ 371 (c)(1), (2), (4) Date: Aug. 11, 2005

(87) PCT Pub. No.: WO2004/016797
PCT Pub. Date: Feb. 26, 2004

(65) Prior Publication Data
US 2006/0006111 A1    Jan. 12, 2006

(30) Foreign Application Priority Data
Aug. 14, 2002 (SE) .................... 02024271

(51) Int. Cl.
C12P 5/02 (2006.01)
C12P 1/04 (2006.01)
C02F 3/00 (2006.01)
B01D 33/048 (2006.01)
C12P 1/00 (2006.01)
C12P 39/00 (2006.01)

(52) U.S. Cl. ............ 435/166; 435/41; 435/42; 435/170; 210/600; 210/603

(58) Field of Classification Search ................. 210/600, 210/603; 435/41, 42, 166, 170
See application file for complete search history.

(56) References Cited

U.S. PATENT DOCUMENTS

| 4,252,901 A * | 2/1981 | Fischer et al. ................. 435/167 |
| 4,386,159 A | 5/1983 | Kanai |
| 4,652,374 A | 3/1987 | Cohen |
| 4,666,605 A | 5/1987 | Minami et al. |
| 5,554,410 A * | 9/1996 | Bell et al. ..................... 426/660 |

(Continued)

FOREIGN PATENT DOCUMENTS

DE    32 27 562 A1    1/1984

(Continued)

OTHER PUBLICATIONS

Britannica Online Encyclopedia, http://www.britannica.com/EBchecked/topic/130867/concentrate Jul. 1, 2010.*

(Continued)

*Primary Examiner* — Jon P Weber
*Assistant Examiner* — Kailash C Srivastava
(74) *Attorney, Agent, or Firm* — Harness, Dickey & Pierce, P.L.C.

(57) ABSTRACT

In a method of producing biogas by anaerobic digestion of organic matter, organic matter is dried to a dry solids content of at least 50% by weight TS and pelletized and then mixed with a liquid to form a slurry. The slurry is contacted with biogas-producing bacteria for digestion under anaerobic conditions in a reactor (102) while producing biogas.

9 Claims, 5 Drawing Sheets

U.S. PATENT DOCUMENTS 6,296,766 B1 10/2001 Breckenridge
2002/0102673 A1* 8/2002 Zhang et al. .................. 435/167

FOREIGN PATENT DOCUMENTS

| JP | 53-124510 | | 10/1978 |
| JP | 60-183099 | A | 9/1985 |
| JP | 09-290239 | A | 11/1997 |
| JP | 2002-192191 | A | 7/2002 |
| RO | 83 589 | | 4/1984 |

OTHER PUBLICATIONS

Fox et al., In "Fermentation and Biochemical Engineering Handbook Principles, Process Design, and Equipment", Second Edition, Vogel et al (Eds.) 1997, Noyes Publications, Westwood, New Jersey, USA, pp. 706-733.*
Hills et al. 1981. Anaerobic Digestion of Dairy Manure and Field Crop Residues. Agricultural Wastes, vol. 3, pp. 179-189.*
Nelson et al. 1939. Effect of Temperature of Digestion, Chemical Composition, and Size of Particles on Production of Fuel Gas From Farm Wastes. Journal of Agricultural Research, vol. 53, pp. 273-287.*
Svenska Renhållningsverks—Föreningen, Publ 91:10, "Biologisk Förgasning Av Hushållsavfall", Naturvårdsverket Rapport 3982; 1991; ISBN 91-620-3982-2 and Partial Translation.
Brummeler et al., "Dry Anaerobic Batch Digestion of the Organic Fraction of Municipal Solid Waste", J. Chem. Tech. Biotechnol. 1991, 50, 191-209.
Vasudevan et al., "Advances in solid state anaerobic digestion of organic wastes", Nat. Acad. Sci. Letters, vol. 20, No. 7 & 8, 1997.
International Search Report for Corresponding PCT Application PCT/SE 03/01177 dated Sep. 9, 2003.
Office Action dated Jul. 14, 2009 in corresponding U.S. Appl. No. 10/524,192.
Angelidaki, I., et al., "Methods for increasing the biogas potential from the recalcitrant organic matter contained in manure," Water Science and Technology, vol. 41, No. 3, pp. 189-194, 2000.
Hills, D. et al., "Effects of Particle Size on Anaerobic Digestion of Tomato Solid Wastes," Agricultural Wastes, vol. 0141-4607, pp. 285-295, 1984.

* cited by examiner

METHOD AND APPARATUS FOR PRODUCTION OF BIOGAS FROM AN ORGANIC MATERIAL

PRIORITY STATEMENT

This application claims priority under U.S.C. §119 to PCT Application No. PCT/SE03/01177, filed Jul. 7, 2003, which claims priority to SE 0202427-1, filed Aug. 14, 2002, the entire contents of each being incorporated herein by reference.

FIELD OF THE INVENTION

The present invention relates to a method of producing biogas by anaerobic digestion of an organic material or organic matter.

The present invention also relates to a device for producing biogas by anaerobic digestion of organic matter, said device comprising a sealable, essentially gas-tight reactor having an inlet for organic matter and outlets for produced biogas and formed digested sludge.

BACKGROUND ART

Digestion of organic waste is utilised in a plurality of processes for reducing volumes of waste and simultaneously producing biogas. In digestion, the organic waste is mixed with a culture of bacteria and is then digested under anaerobic conditions. In digestion, the organic waste is decomposed, thus producing biogas, which essentially consists of methane and carbon dioxide, and digested sludge.

U.S. Pat. No. 4,652,374 in the name of Cohen discloses a method of digesting organic waste in two steps. The solid organic waste is ground in such a manner that 80% has a particle size of 0.25-1.5 mm. Hydrolysis/acidification takes place in a first step. The liquid from the first step is separated and supplied to a second step where the main production of methane takes place.

U.S. Pat. No. 4,386,159 in the name of Kanai discloses a method of digesting organic waste matter with a certain ratio of carbon to nitrogen. The organic waste matter is ground to a juice-like liquid and is then mixed with a bacteria-containing sludge in a tank. Then the digestion is allowed to proceed in the tank without agitation for about 5-7 days.

It is a disadvantage in the above processes that the production of biogas is inefficient and that the biogas therefore will be expensive.

SUMMARY OF THE INVENTION

An object of the present invention is to provide a method of producing biogas, in which method the above drawbacks are eliminated or significantly reduced, and thus to provide a method of producing biogas in a more efficient way.

More specifically, the invention provides a method of producing biogas by anaerobic digestion of organic matter, which method is characterised by drying organic matter to a dry solids content of at least 50% by weight TS and subsequently pelletising the same, mixing the pelletised organic matter with a liquid to form a slurry, contacting the slurry with biogas-producing bacteria for digestion under anaerobic conditions in a reactor, and digesting the slurry while generating biogas.

The invention also relates to a device for producing biogas by anaerobic digestion of organic matter, said device comprising a sealable, essentially gas-tight reactor having an inlet for organic matter and outlets for produced biogas and formed digested sludge, which device is characterised in that it comprises a premixing tank for mixing organic matter dried to a dry solids content of at least 50% by weight TS and pelletised, with a liquid to a slurry, and a feed pipe for feeding the slurry to the reactor.

Further advantages and features of the invention will be evident from the following description and the appended claims.

BRIEF DESCRIPTION OF THE DRAWINGS

The invention will now be described in more detail by way of non-limiting embodiments and with reference to the accompanying drawings.

DETAILED DESCRIPTION OF THE INVENTION

Figure 1:
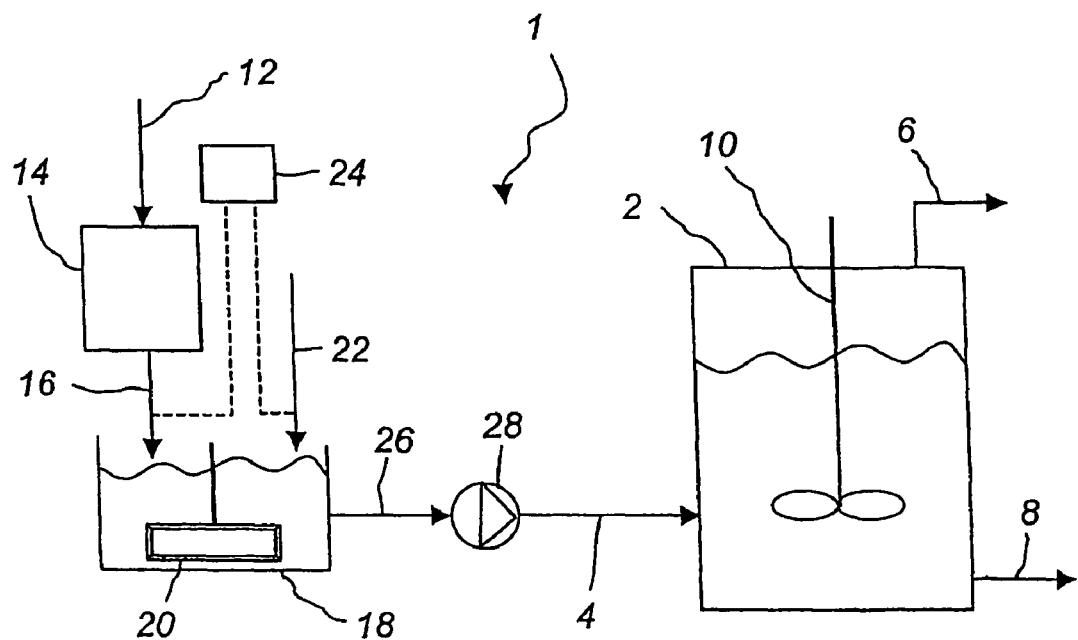
FIG. 1 illustrates a device for producing biogas according to a first embodiment of the invention.

In the present application, the unit "% by weight TS" relates to the dry solids content (total solids) of a material. The dry solids content of a material is measured according to Swedish standard SS 02 81 13 by the material being weighed before measuring and then being heated at 105° C. for 20 h so that water evaporates. The material is then weighed once more. The dry solids content in % by weight TS is then calculated as follows $$\% \text{ by weight } TS = \frac{\text{weight after heating at } 105° \text{ C.}}{\text{weight before heating}} * 100\%$$

For instance, 90% by weight TS relates to a material where 90% of the original weight of the material remains after heating the material at 105° C. for 20 h.

In the present application, the unit "% by weight VS" relates to the content of volatile organic matter of a material, below called the volatile solids content. To determine the volatile solids content, first the dry solids content of the material is determined and then its fixed solids. The fixed solids can be determined according to Swedish Standard SS 02 81 13 by a material which has been evaporated at 105° C. for 20 h as stated above being calcined for 2 h at 550° C. The volatile solids content relates in the present application to the dry weight of the material, i.e. the weight after evaporation at 105° C. for 20 h, reduced by the fixed solids and then divided by the dry weight of the material, i.e. the weight after evaporation at 105° C. for 20 h. The volatile solids content of the material in % by weight VS is thus calculated as follows:

$$\% \text{ by weight } VS = \frac{\text{weight after } 105° \text{ C.} - \text{weight after } 550° \text{ C.}}{\text{weight after } 105° \text{ C.}} * 100\%$$

For instance, a volatile solids content of 85% by weight VS means that 85% of the dry weight of the material, i.e. the weight of the material after heating at 105° C. for 20 h, consists of organic, volatile compounds while 15% consists of fixed solids.

The unit "g of volatile solids per day" relates, analogously with the unit % by weight VS, to an amount of volatile organic matter in grams per day as stated above. The amount of volatile organic matter supplied to the reactor, i.e. g of volatile solids, determines how much biogas can be produced since the biogas is produced from the volatile organic matter (and not from the fixed solids or the water contents).

By "degree of digestion" is meant, in the present application, the amount of material supplied to a digestion reactor that is converted into biogas in the digestion chamber. If, for instance, 10 g of volatile solids per day is supplied to a reactor in the form of digestible material and the digested sludge removed from the reactor contains correspondingly 2 g of volatile solids per day, the degree of digestion is 80%. The bacteria entrained by removed digested sludge contain some g of volatile solids, and therefore a degree of digestion of 100% according to the above definition cannot be achieved in practice.

According to the invention, a dried, pelletised and suitably ground organic matter in contact with biogas-producing bacteria is digested to produce biogas. The dried, pelletised and suitably ground organic matter increases the production of biogas and makes it possible to produce a certain amount of biogas in a smaller reactor than has previously been possible. Thus, biogas can be produced at a lower cost by means of the present invention.

A preferred example of organic matter which is suited for use in the present invention is green matter. In the present invention, green matter relates to plants of the type using photosynthesis for producing the plant matter. The green matter can advantageously consist of various agricultural products, such as ensilage, straw, grain, grain offal, rape, sugar-beets, turnips, maize, sunflowers, cabbage, potatoes, molasses, peas, beans, lentils, flax, lupins and pasture plants, such as lucerne, grass and clover. Agricultural products are often available in large amounts and frequently have a high energy content. Moreover, the agricultural products often have a content of nutrients and trace elements making the produced digested sludge most convenient for use as fertiliser on arable land. A further advantage of the above-mentioned agricultural products is that they do not contain any harmful bacteria. Thus, the heating to at least 70° C. for at least 1 h, referred to as sanitation, which is necessary, for instance, in connection with domestic waste and slaughterhouse waste, can be omitted, resulting in reduced production costs. Also products such as lawn waste, straw from edges of roadways, natural hay and leaves, which normally arise in municipal activities, can be used in digestion.

The organic matter is dried before digestion. Many of the above examples of green matter have a dry solids content of only 15-35% by weight TS. The drying of the green matter has several advantages. In addition to the digestion in the reactor becoming more efficient, it will also be easier to transport and store the green matter. Consequently, the green matter can be harvested and dried at a time of the year when the supply of green matter is good so as then to be digested during an extended period. The dried green matter is also considerably less expensive to transport since a large amount of water has been removed.

Green matter should be dried to a dry solids content of at least 50% by weight TS. Drying to at least 70% by weight TS, still more preferred at least 80% by weight TS, has been found to result in still more efficient digestion in the reactor and reduces the amount of water supplied to the reactor.

The digestion in the digestion chamber will be most efficient if the organic matter is ground before being introduced into the digestion chamber. Grinding makes the matter more available to the biogas-producing bacteria and thus accelerates digestion. Green matter can be ground before the above-mentioned drying. Such grinding of "wet" matter, however, is quite difficult to carry out and often results, in particular with green matter having a low dry solids content, in a slurry that is difficult to handle. For this reason, it is often preferred first to dry the green matter and then grind it to the desirable particle size. A suitable particle size of the ground matter from the point of view of digestion has been found to be about 0.5-3 mm, i.e. the major part, at least about 80% by weight, of the matter should have a particle size in this range after grinding. Grinding to smaller particle sizes, for instance below 0.1 mm, increases the dusting problems and increases the consumption of energy in grinding without making digestion significantly quicker. With larger particle sizes of the ground matter, such as larger than 5 mm, the digestion process will be slower, thus requiring a larger reactor. In some cases, for instance with compact green matter such as potatoes, sugar-beets and cabbage, it is convenient to cut the green matter into flakes, for instance flakes with a size of 10-30 mm, before the green matter is dried to achieve maximum efficiency in the drying process. An example of a type of drier which is suitable for drying of green matter is a rotary oven. Drying of green matter may also be preceded by dewatering, which can be carried out, for instance, by means of a filter press, for the purpose of reducing the amount of water that must be removed from the green matter in the actual drying.

It has been found particularly convenient to pelletise the green matter after drying. Pelletising changes the dried green matter into a form which is easy to handle and transport. Thus, green matter can be dried and pelletised locally and transported to large-scale regional plants for producing biogas. A further advantage is that different types of pelletised green matter can easily be dosed in the desired proportions to the reactor to achieve a chemical composition in the reactor which gives the biogas-producing bacteria good conditions for growth. Consequently, pelletised green matter with different contents of minerals, such as phosphorus and potassium, can be mixed in such a manner that optimal conditions for bacteria are ensured and that digested sludge with a suitable composition to be returned to agriculture is obtained. When using pelletised green matter, it is preferable to grind the pellets before being introduced into the reactor. In the actual pelletising, a certain degree of compacting of the dried green matter is effected. Grinding makes the pelletised matter more available to the biogas-producing bacteria and increases the rate of digestion. Since the pelletised matter has in many cases already been ground before the actual pelletising, a mill for grinding of pellets can be made relatively simple. The above ranges of particle sizes for grinding of the dried organic matter also apply to grinding of pellets.

When the dried, suitably pelletised and suitably ground organic matter is to be introduced into a reactor, the matter is mixed with a liquid to form a slurry. The slurry can be produced in various ways. A preferred way of producing a slurry is to mix the dried and suitably ground organic matter with water, for instance tap water, lake water, condensate, purified waste water or some other water-containing liquid which with regard to biogas production is suitable for supply to the reactor. Thus, also water-containing liquids of little value, or being considered as waste, can thus be used to produce the slurry. According to this method, matter, which has suitably been ground, is mixed with water in a premixing tank, which is provided with a powerful agitator operating at a low speed. The premixing tank reduces the risk of air being unintentionally introduced into the reactor and makes it easier to control the amount of matter that is introduced into the reactor. The premixing tank also provides wetting of the dried organic matter, which results in digestion beginning more quickly in the reactor. A control system is used to achieve the desired dry solids content of the slurry in the premixing tank. Preferably, a batch method for mixing the slurry is used. The residence time in the premixing tank suitably is relatively short, about 5-50 min. However, in some cases also continuous methods may be used. It is desirable not to introduce large amounts of water into the reactor since the residence time and, thus, the degree of digestion would then be reduced. A small amount of supplied water also involves a low cost for heating of supplied water to the desired digestion temperature. It has been found that by means of dried and ground organic matter in general, it is possible to produce pumpable slurries with a dry solids content of up to about 35% by weight TS. With grain, grain offal, and pellets of grain offal it is possible to obtain pumpable slurries with a dry solids content of up to 45% by weight TS. The high dry solids content brings several advantages. On the one hand, only little water has to be added. Thus the consumption of water will be low and the residence time in the reactor will be long, which results in a good degree of digestion. A further advantage of a small amount of water being added is that the produced digested sludge will have a high dry solids content, which facilitates handling, reduces the cost of transport and increases the value of the digested sludge as fertiliser. The high dry solids content also reduces the pumping work required to pump the slurry into the reactor and makes it possible to dimension premixing tank, pumps and pipes for smaller flows. An advantage of using essentially pure water when producing the slurry is that the mixing can be carried out in an open premixing tank. This makes the tank cheap to manufacture and simple to monitor. It has been found that the slurry suitably should have a dry solids content of 15-45% by weight TS, still more preferred 15-40% by weight TS and most preferred 25-35% by weight TS. Compared with digestion of e.g. cow-dung, according to prior-art technique, where the dry solids content of the slurry introduced is only about 6-8% by weight TS, it is possible, in the invention with the same residence time in the reactor, to extract the same amount of biogas from a reactor having only about one-fourth of the volume required in digestion according to prior art. The high degree of digestion for pelletised organic matter, in particular pelletised agricultural products, in the method according to the invention implies that a very large part of the volatile solids content of the slurry supplied to the reactor will be decomposed into biogas. For this reason, the reactor in which digestion takes place will contain digested sludge with a dry solids content of typically 5-10% by weight TS although the slurry supplied to the reactor from the premixing tank has a considerably higher dry solids content. It is an advantage that the digested sludge in the reactor has a considerably lower dry solids content than the supplied slurry since agitation in the reactor is facilitated and the supplied pelletised organic matter's availability to the bacteria is increased, which contributes to the high degree of digestion.

Another preferred method of producing a slurry is to discharge digested sludge from the reactor and mix this with the dried and suitably ground organic matter in a premixing tank to form a slurry which is then introduced into the reactor. An advantage of using digested sludge is that no water in addition to the small amount of residual moisture that is present in the dried organic matter has to be added. Therefore the residence time in the reactor will be long. Since the digested sludge contains bacteria, a certain production of biogas will already take place in the premixing tank, which suitably has a residence time of about 5-50 min. For this reason, the premixing tank should be an essentially gas-tight container which continuously is vented to prevent explosive gas mixtures from being produced when produced biogas and air accompanying the ground matter are mixed. It is desirable to minimise the energy that is consumed to pump digested sludge to the premixing tank and to pump the slurry prepared from dried organic matter and digested sludge to the reactor. As mentioned above, the dried organic matter allows preparation of pumpable slurries with a very high dry solids content. It has been found that the slurry should have a dry solids content of 15-45% by weight TS, still more preferred 15-40% by weight TS, and most preferred 25-35% by weight TS. Of the dry solids content in the slurry, about 3-6% by weight TS originates from the digested sludge, and therefore the amount of slurry which, at a given dry solids content of the slurry produced and a given amount of dried organic matter, must be pumped to the reactor will be slightly greater compared with the above-described mixing with pure water.

A further alternative is to use in the preparation of the slurry a suitable reject water, i.e. a liquid that arises as a residual product in another process. An example of such reject water that can be used is reject water from sludge dewatering in wastewater treatment plants. Such reject water contains, inter alia, potassium and nitrogen that may serve as extra nutriment for the biogas-producing bacteria and, thus, increase the efficiency of the biogas production while at the same time disposing of the reject water which is to be regarded as waste.

It has been found that dried and suitably ground organic matter, in particular dried and ground agricultural products, is very convenient for increasing the biogas production in existing digestion plants. There are a large number of existing digestion plants digesting, for instance, cow-dung, slaughterhouse waste, sorted-out household waste (the part suitable for composting), food waste and sludge from wastewater treatment plants. The purpose of these existing plants is usually to remove waste that is difficult to handle. These plants often digest matter with a low dry solids content and a low energy content per tonne of waste. As a result, the production of biogas will be small. The formed digested sludge has a low dry solids content and is therefore difficult to handle. According to the invention, dried, suitably pelletised and suitably ground organic matter is supplied to such a plant. The dried, pelletised and ground matter adds a very small amount of liquid to the existing plant. This has the advantage that the residence time in the existing reactor is not reduced significantly. This means that the degree of digestion, i.e. the amount of the supplied matter that is converted during the digestion process, will not decrease. The supplied dried, pelletised and suitably ground organic matter has a high energy content per kg and will considerably increase the biogas production in the plant. The dry solids content of the removed digested sludge increases owing to more matter being introduced into the reactor. This makes the digested sludge easier to handle. The introduced dried organic matter will also increase the nutritive value of the digested sludge, thereby increasing its value as fertiliser. The extra nutriment which thanks to the dried organic matter is added to the biogas-producing bacteria can make the bacteria more active by co-digestion, i.e. the nutrients of the digested matters supplement each other, which may result in an increased degree of digestion. The extra equipment that is needed to make an existing digestion process more efficient in the manner described above is simple because the dried matter is easy to handle. Thus, by means of the invention the biogas production can be increased and the handleability of the digested sludge be simplified and its value increased in an existing digestion plant. It will be appreciated that the dried organic matter can also be used in plants which from the beginning are built to digest dried, suitably pelletised and suitably ground organic matter together with other organic matter, which, for instance, can be water treatment sludge, cow-dung or waste that is desired to be removed.

In the type of plants where the dried organic waste is used to increase the efficiency of an existing plant, the dried, suitably pelletised and suitably ground organic matter is suitably mixed with a liquid to form a slurry which is then introduced into the reactor. At least 10% by weight of the totally supplied dry solids should originate from the dried, pelletised and ground organic matter, i.e. for 1 tonne of dry solids supplied to the reactor, at least 100 kg should be dry solids originating from the dried organic matter. Still more preferred, at least 30% by weight of the totally supplied dry solids should originate from the dried, suitably pelletised and suitably ground organic matter. It is desirable to prevent large amounts of slurry or sludge to be circulated in the plant. Circulation of large amounts of slurry causes increased consumption of energy and may also cause interruptions in the digestion process. Thus, it is suitable to produce a slurry having a relatively high dry solids content. Slurry can be produced in many different ways. A preferred method is to remove digested sludge from the reactor and mix it with the dried and ground organic matter in a premixing tank. The slurry formed in the premixing tank is then supplied to the reactor. This has the advantage that no extra water besides the small amount of residual moisture that exists in the dried organic matter is supplied to the reactor. Another preferred method is to mix the dried organic matter with the organic matter of a different type, i.e. the cow-dung, the water treatment sludge etc, which is also digested in the reactor. This method is in many cases very cost-efficient since an existing tank can be used as premixing tank. Also in this method, no extra water is supplied in addition to the small amount of residual moisture that is present in the dried organic matter. A further method is to mix the dried organic matter with pure water in a separate premixing tank. However, this increases the amount of water that is supplied to the reactor where the dried organic matter is digested together with organic matter of a different type, such as cow-dung, water treatment sludge. In the cases when pure water must be supplied to the reactor anyway, this water can suitably be used to prepare the slurry with a high dry solids content.

A particularly suitable method of using dried, pelletised organic matter, such as pelletised grain offal which mainly consists of husks and rejected grains from harvesting and threshing of grain, in a process where another material is digested aims at controlling the biogas production. Momentary adding of a certain amount of pelletised grain offal will increase the biogas production with a very short time delay. When the demand for biogas increases in an expected or unexpected manner, pelletised grain offal can thus be supplied to a reactor digesting, for instance, sewage sludge in order to meet the increased demand. Owing to pelletised grain offal being easily decomposable, the biogas production will increase very quickly, thus making it possible to meet the increased demand. An example is a plant digesting sewage sludge and producing biogas which is used in local busses. On weekdays, the demand for biogas is great and therefore pelletised grain offal as well as sewage sludge is supplied to the reactor on weekdays. On the last weekday before a weekend, the supply of pelletised grain offal is stopped and the biogas production decreases quickly, typically after 4-24 h, to a low level corresponding to the biogas production that is consumed by the local busses during the weekend. Just before the end of the weekend, the supply of pelletised grain offal is started again, so that the biogas production again reaches the level which is suitable on weekdays. In this way, a plant is provided, which continuously takes care of and digests sewage sludge and which in periods with a great demand for biogas also digests pelletised grain offal. It is, of course, also possible to use other pelletised organic matters to control the biogas production. The pelletised matters are suitably such as are relatively easily decomposable so that the biogas production increases quickly after the pellets in question being added.

Digestion is conveniently carried out as a continuous or semicontinuous process by means of a tank reactor which will be described in more detail below, or by means of a tube reactor which is also called plug flow reactor. At a first end of the tube reactor, dried green matter, for instance in the form of pellets, and a bacteria culture, which for instance can be present in the form of recirculated digested sludge, are introduced, digested sludge and biogas being discharged at a second end of the tube reactor, said second end being located downstream of the first end of the tube reactor. The method can also be carried out in a batch reactor.

For the anaerobic digestion to function, air is not allowed to come into contact with the sludge during digestion. A reactor for use in the method according to the invention must thus be air-tight. The reactor is provided with an inlet for slurry prepared from dried and suitably ground organic matter and outlets for digested sludge and biogas, said inlet and outlets being designed so that no air can enter the reactor.

Dried and suitably ground green matter is digested suitably for an average residence time of about 5-100 days, preferably about 40-60 days. A longer residence time improves the degree of digestion to some extent, but at the same time the quantity of organic matter that can be introduced into the reactor is reduced.

Digestion takes place at a temperature of 30-65° C. A higher temperature usually results in quicker digestion. At the same time the heating costs increase and the time that is available for taking care of any problems in the process is reduced. Certain bacteria cultures also have a production maximum which is lower than the above-mentioned upper temperature range. It has therefore been found that a temperature in the range 36-40° C. is particularly preferred in the present invention. It is suitable to make an adjustment between residence time, temperature and degree of digestion and use the most economical combination of these factors.

In digestion in a tank reactor, the dry solids content of the digested sludge in the reactor is suitably about 4-30% by weight TS, preferably about 5-10% by weight TS. In an agitated and continuously operating tank reactor, the digested sludge removed from the reactor will have essentially the same dry solids content as the digested sludge in the reactor. Supply of new slurry to the tank reactor is thus made continuously, i.e. as an even inflow, or semicontinuously, i.e. in small portions, preferably from a premixing tank. Removal of sludge from the tank reactor can be effected continuously, i.e. as an even outflow, or semicontinuously, i.e. in small portions.

When starting the process, an active culture of bacteria is usually introduced into the reactor. This culture of bacteria may consist of, for instance, digested sludge from a parallel digestion plant, digested sludge from a municipal wastewater treatment plant or cow-dung. As the culture of bacteria grows, an increasingly greater amount of the slurry of dried, suitably pelletised and suitably ground organic matter can be supplied to the reactor. Too quick an increase of the amount of supplied organic matter is prevented by measuring at short intervals the content of volatile fatty acids in the digested sludge and ensuring that the content of volatile fatty acids is kept at a desirably low level by regulating the supply of organic matter.

The method according to the invention can be carried out in a plurality of reactors connected in series. However, it is particularly advantageous to carry out the anaerobic digestion in a single step since this saves equipment and maintenance costs.

DESCRIPTION OF PREFERRED EMBODIMENTS

FIG. 1 shows a first embodiment of a device 1 for producing biogas. The device 1 has a container in the form of an essentially gas-tight reactor 2. The reactor 2 has an inlet 4 for organic matter, an outlet 6 for produced biogas and an outlet 8 for formed digested sludge. An agitator 10 keeps the matter in the reactor agitated.

Grain which has been dried to a dry solids content of 92% by weight TS is supplied from a storage silo (not shown) through a feed pipe 12 to a mill 14. In the mill 14, the grain is ground to an average particle size of about 1 mm. The ground grain is supplied through a feed pipe 16, which may consist of, for instance, a screw conveyor, to a premixing tank 18. The premixing tank 18, which is an open tank, has a low speed agitator 20. The agitator 20 is a scraper-type agitator and may conveniently resemble the agitators that are used in the baking industry for preparing dough. A water supply pipe 22 is arranged to supply essentially pure process water to the premixing tank 18. A control system 24 is arranged to batch feed water through the pipe 22 and ground grain through the pipe 16 to the premixing tank 18 in such proportions that a dry solids content of 35% by weight TS is obtained in the premixing tank 18. Use is suitably made of a weighing cell (not shown) which is arranged under the premixing tank 18, to control the supply of water and grain to the premixing tank 18. When a slurry of grain and water has been mixed to an even consistency in the premixing tank 18, the slurry is pumped through a pipe 26 by a pump 28 to the inlet 4 of the reactor 2 and into the reactor 2. To obtain an even liquid volume in the reactor 2, a corresponding amount of digested sludge is pumped out through the outlet 8. The reactor 2 thus is a continuously or semicontinuously operating, agitated tank reactor which contains digested sludge with a dry solids content of about 5-10% by weight TS.

Figure 2:
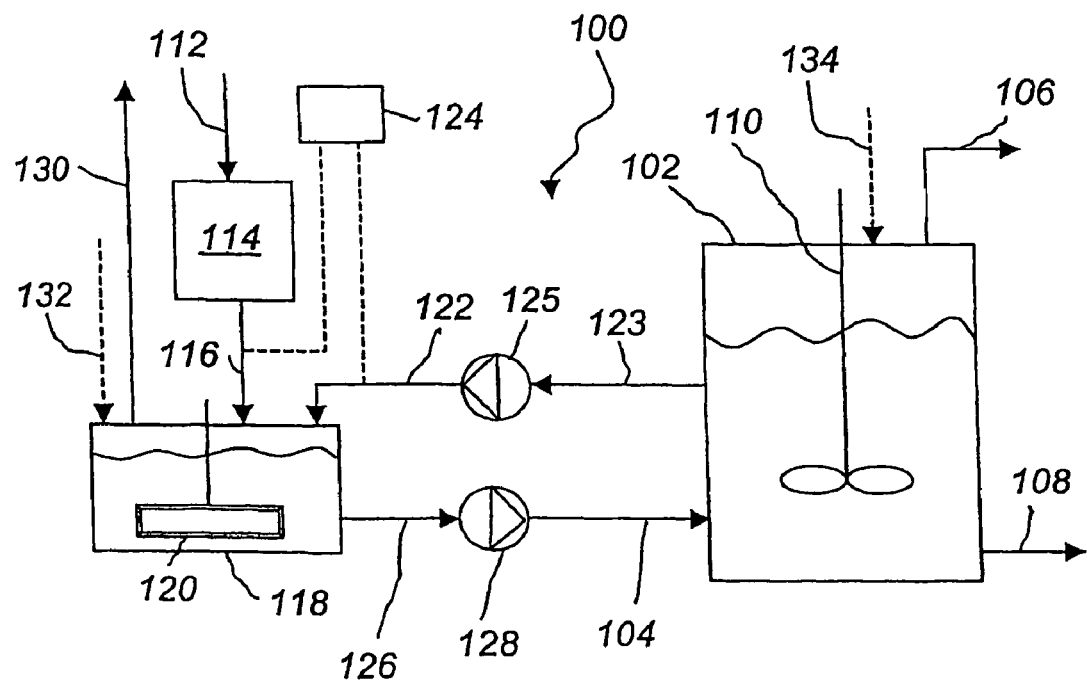
FIG. 2 illustrates a device for producing biogas according to a second embodiment of the invention.

FIG. 2 shows a different embodiment of the invention in the form of a device 100. The device 100 has an essentially gas-tight container in the form of a reactor 102 which has an inlet 104 for organic matter, an outlet 106 for produced biogas, an outlet 108 for formed digested sludge and an agitator 110 of essentially the same design as those shown in FIG. 1.

Dried and pelletised green matter is passed from a storage silo (not shown) through a feed pipe 112 to a mill 114. In the mill 114, the pellets are ground to an average particle size of about 1 mm. The ground pellets are fed through a feed pipe 116 to a premixing tank 118. The premixing tank 118, which is an essentially gas-tight container, has a low speed agitator 120. A liquid supply pipe 122 is arranged to supply, by means of a pipe 123 and a pump 125, digested sludge from the reactor 102 to the premixing tank 118. A control system 124 is arranged to batch feed digested sludge through the pipe 122 and ground pellets through the pipe 116 to the premixing tank 118 in such proportions that a dry solids content of at least 15% by weight TS is obtained in the premixing tank 118. When a slurry prepared from pellets and digested sludge has been mixed to an even consistency in the premixing tank 118, the slurry is pumped through a pipe 126 by a pump 128 to the inlet 104 of the reactor 102 and into the reactor 102. To obtain an even liquid volume in the reactor 102, a corresponding amount of digested sludge is pumped out through the outlet 108. In the premixing tank 118, a certain amount of biogas will be produced during the mixing process. A gas pipe 130 conducts this gas, which consists of a mixture of produced biogas and the air which has unintentionally been supplied through the feed pipe 116, to a biofilter (not shown) which decomposes methane and odorous gases. If it is necessary to be able to keep the dry solids content in the reactor 102 at a desirable level, pure process water can be supplied to dilute the sludge in the reactor. This process water can either be supplied to the premixing tank 118 through a pipe 132 or directly to the reactor 102 through a pipe 134.

Figure 3:
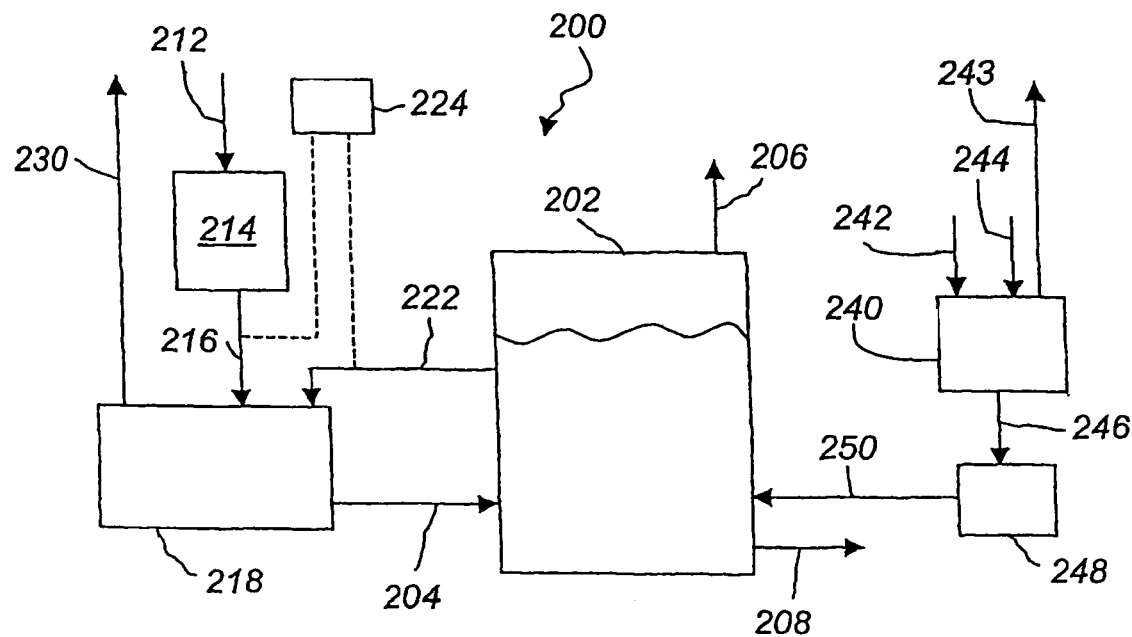
FIG. 3 illustrates a device for producing biogas according to a third embodiment of the invention.

FIG. 3 is a schematic view of a third embodiment of the invention in the form of a device 200. The pumps and agitators are not shown in FIG. 3, but it will be appreciated that such components are used in essentially the same way as illustrated in FIGS. 1 and 2. The device 200 digests a mixture of cow-dung, which is supplied to a mixing tank 240 through a pipe 242, and slaughterhouse waste, which is supplied to the mixing tank 240 through a pipe 244. The mixing tank 240 is a closed tank which by means of a gas pipe 243 is vented to a biofilter (not shown) which decomposes methane and odorous gases. The mixture obtained in the mixing tank 240 is passed through a pipe 246 to a sanitation tank 248 where the mixture is heated to at least 70° C. for at least 1 h for the purpose of killing harmful bacteria. The sanitised mixture, which has a dry solids content of about 4-12% by weight TS, is passed through a pipe 250 from the sanitation tank 248 to a reactor 202, which is of a type similar to the reactor 102 as described above and thus has, among other things, an outlet 206 for produced biogas and an outlet 208 for formed digested sludge.

With a view to improving the biogas production in the device 200, dried grain is fed through a feed pipe 212 to a mill 214 where the grain is ground to an average particle size of about 1 mm. The ground grain is fed through a feed pipe 216 to a premixing tank 218 which is of essentially the same type as described above regarding the premixing tank 218. A liquid supply pipe 222 is arranged to feed digested sludge from the reactor 202 to the premixing tank 218. A control system 224 is arranged to batch feed digested sludge through the pipe 222 and ground grain through the pipe 216 to the premixing tank 218 in such proportions that a dry solids content of 35% by weight TS is obtained in the premixing tank 218. When a slurry prepared from grain and digested sludge has been mixed to an even consistency in the premixing tank 218, the slurry is pumped from the premixing tank 218 to the reactor 202 through an inlet 204. A gas pipe 230 conducts gas, which is generated in the mixing in the premixing tank 218, to a biofilter (not shown) which decomposes methane and odorous gases.

Figure 4:
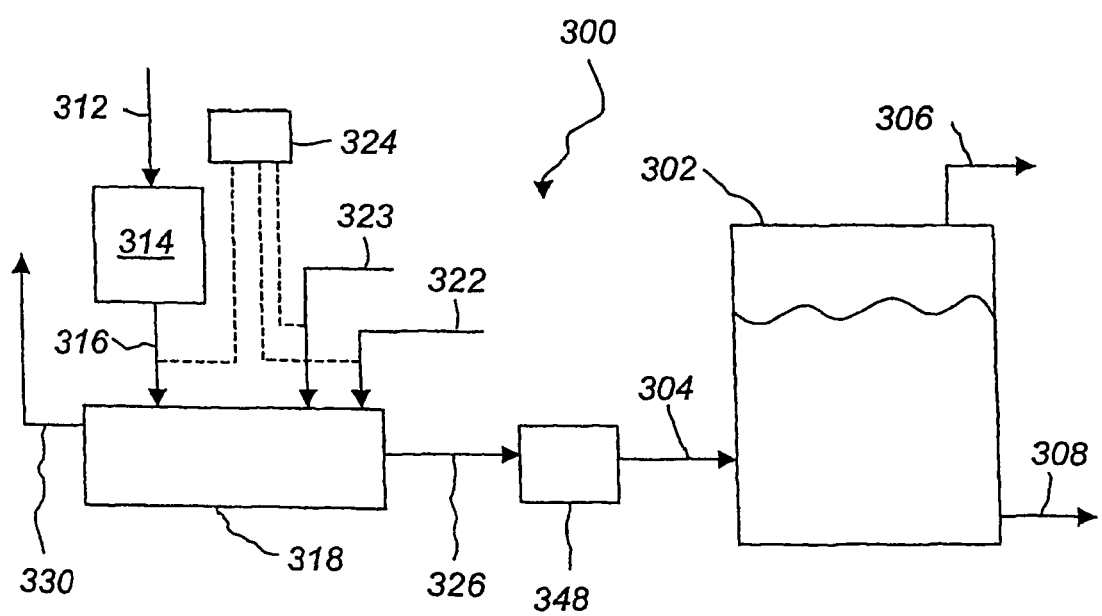
FIG. 4 illustrates a device for producing biogas according to a fourth embodiment of the invention.

FIG. 4 shows schematically a fourth embodiment of the invention in the form of a device 300. The pumps and the agitators are not shown in FIG. 4, but it will be appreciated that such components are used in essentially the same way as illustrated in FIGS. 1 and 2. The device 300 digests cow-dung and meat waste. The cow-dung and the meat waste are fed through a pipe 322 and a pipe 323, respectively, to an essentially gas-tight tank 318 and are mixed.

With a view to improving the biogas production in the device 300, dried and pelletised green matter is fed through a feed pipe 312 to a mill 314 where the pellets are ground to an average particle size of about 1 mm. The ground pellets are fed through a feed pipe 316 to the tank 318, which in the device 300 thus is used as premixing tank and is of essentially the same type as described above regarding the premixing tank 118. A certain amount of biogas will be produced in the premixing tank 318 in the mixing process. A gas pipe 330 conducts gas, which consists of a mixture of produced biogas, air unintentionally supplied through the feed pipe 316 and gases generated by the cow-dung and the meat waste, from the tank 318 to a biofilter (not shown) which decomposes methane and odorous gases. A control system 324 is arranged to batch feed cow-dung and meat waste through the pipes 322, 323 and ground pellets through the pipe 316 to the premixing tank 318 in such proportions that a dry solids content of at least 15% by weight TS is obtained in the premixing tank 318. When ground pellets, cow-dung and meat waste have been mixed to a slurry with an even consistency in the premixing tank 318, this slurry is pumped from the premixing tank 318 through a pipe 326 to a sanitation tank 348 where the slurry is heated to at least 70° C. for at least 1 h for the purpose of killing the harmful bacteria that may exist in the slaughterhouse waste. The sanitised slurry is pumped from the sanitation tank 348 through an inlet 304 into a reactor 302 which is of a type similar to the reactor 2 as described above and thus has, inter alia, an outlet 306 for produced biogas and an outlet 308 for formed digested sludge.

It will be appreciated that many variations of the embodiments described above are feasible within the scope of the invention as defined by the appended claims.

Example 1

Figure 5:
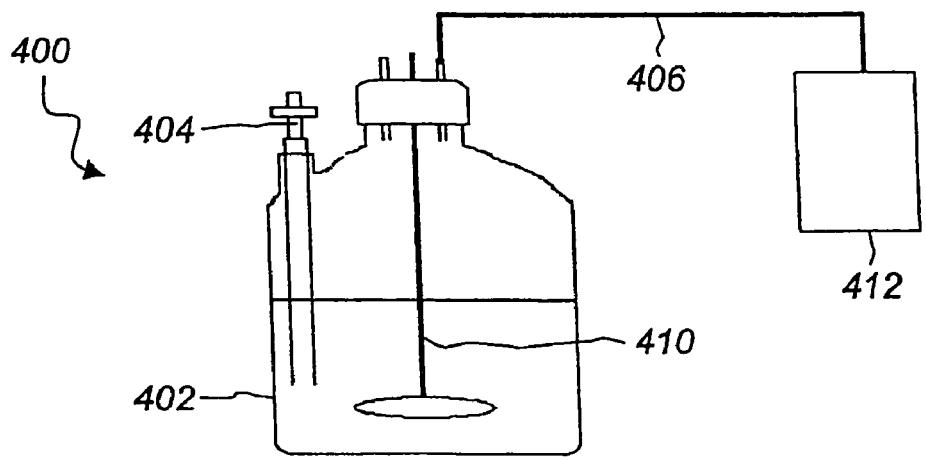
FIG. 5 is a schematic view of a device which has been used in exemplary digestion experiments.

In a digestion experiment involving grain, an experimental device 400 which is shown in FIG. 5 was used, said device 400 having a gas-tight glass reactor 402 with a volume of 5 l. The liquid volume in the reactor 402 was kept constant at 3 l. A propeller agitator 410 (with a speed of 300 rpm) was used to achieve complete agitation in the reactor 402. A pipe 406 passed generated gas from the reactor 402 to a gas meter 412 measuring the volume of generated gas. A tight glass feed-through 404 was used for batch supply of grain and intermittent removal of formed digested sludge. A tempered space (not shown) was used to keep the temperature in the glass reactor 402 at 37° C.

When starting the experiment, 3 l of digested sludge from a full-scale digestion plant was introduced into the reactor 402. The sludge that was digested in the full-scale plant was of the origin that is evident from Table 1.

TABLE 1

Origin of materials in full-scale plant.

| Supplied product | Unit by volume % by volume |
|---|---|
| Cow-dung | 5.4 |
| Slaughterhouse waste | 72.7 |
| Others* | 21.9 |
| Total: | 100 |

*"Others" includes above all waste from food production and waste from large-scale kitchens.

When starting the experiment, the reactor 402 thus contained active digested sludge including an active culture of biogas-producing bacteria.

10 g grain was charged to the reactor 402 daily. The grain consisted of 50% rye and 50% wheat and was present in the form of whole and screened grains. The grain was ground in a laboratory mill of the type Retsch Mühl type SR2 delivered by Retsch GmbH, DE, to a particle size of about 1 mm. The dry solids content of the ground grain was 91.6% by weight TS and the volatile solids content was 96.7% by weight VS. Thus, each day 8.68 g of volatile solids was charged, which corresponded to about 3 g of volatile solids per litre of reactor liquid and day. The ground grain was mixed with 18 ml water to a substrate mixture with a dry solids content of 35% by weight TS and a volume of 25 ml. For practical reasons, it was necessary to dilute the substrate mixture with digested sludge to be able to introduce it into the reactor 402 through the tight glass feed-through 404 by means of a syringe. For this reason, 100 ml digested sludge was removed daily. 75 ml of this digested sludge was mixed with the substrate mixture and introduced together with the substrate mixture into the reactor 402. The remaining 25 ml of the digested sludge was rejected to keep the volume in the reactor 402 constant. The residence time in the reactor thus was 120 days with the charging stated above.

Figure 6:
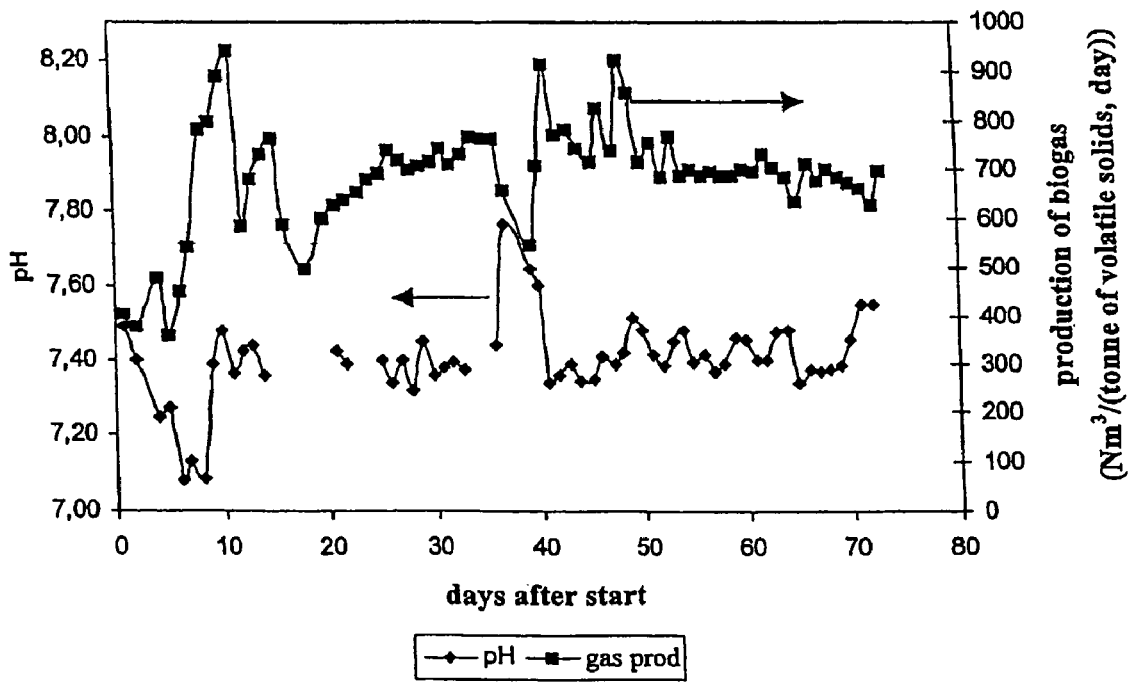
FIG. 6 illustrates the production of biogas per tonne of volatile solids and day in a first exemplary experiment.

FIG. 6 shows the production of biogas in the unit $Nm^3$ of gas per added tonne of volatile solids and day as a function of the number of days after start. As appears from FIG. 6, the production is first somewhat irregular. From day 50, the system is balanced. As appears from FIG. 6, the average production of biogas from day 50 to day 70 is about 700 $Nm^3$ of biogas per tonne of volatile solids and day, "$Nm^3$" relating to $m^3$ of gas at 0° C. and $1.013*10^5$ Pa and "tonne of volatile solids per day" relating to the amount of volatile solids that is charged daily. Calculated on the charged grain, the average production was 616 $Nm^3$ of biogas per tonne of grain and day. Calculated on the dry solids content of charged grain, the average production was 673 $Nm^3$ of biogas per tonne of dry solids and day. The produced biogas was collected at regular intervals and analysed with respect to methane content. In stable production, the methane content was 49-51%. FIG. 6 also shows the pH of the reactor liquid in the experiment. Except for certain disturbances, the pH was relatively stable in the range 7.3-7.5. The removed digested sludge had a dry solids content of 6.6% by weight TS and a volatile solids content of 89.4% by weight VS, corresponding to a degree of digestion of 83%.

Figure 7:
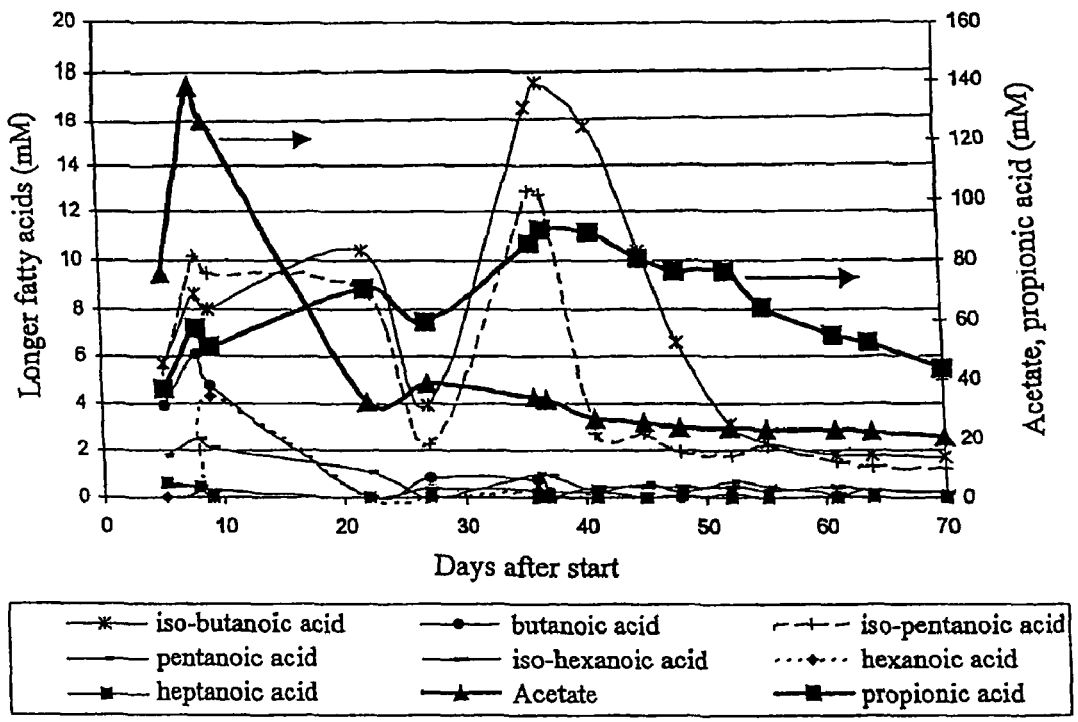
FIG. 7 shows the contents of volatile fatty acids which have been measured in the first exemplary experiment.

FIG. 7 shows the content of volatile fatty acids in the digested sludge as a function of the number of days from start. As is evident, the contents of the various fatty acids vary considerably during the first 50 days of the experiment. In days 50-70, the contents are stabilised. This may be explained by the fact that it takes time for the culture of bacteria, originating from digestion of essentially animal waste, to adapt to the grain. There was also some experiment-related problems at the beginning of the experiment. Round day 70, the contents of all fatty acids are low, indicating that the digestion process is efficient and operates in a stable manner.

Example 2

A device 400 of the type described above was used for the experiment. At the start of the experiment, 3 l of digested sludge was charged from the above-mentioned full-scale plant. The origin of the digested sludge is thus evident from Table 1 above.

The substrate that was supplied to the reactor 402 consisted of grain and pasture plants. The grain consisted of 50% rye and 50% wheat and was present in the form of whole and screened grains. The grain was ground in the above-mentioned laboratory mill to a particle size of about 1 mm. The dry solids content of the ground grain was 91.6% by weight TS and the volatile solids content was 96.7% by weight VS. The pasture plants consisted of a mixture of clover and grass and had a dry solids content of 30.8% by weight TS and a volatile solids content of 92.2% by weight VS.

Four days a week, only ground grain was supplied to the reactor 402. The supply of grain amounted to 11.1 g, corresponding to 10 g of volatile solids. The supply of grain was carried out by mixing grain and water to a dry solids content of 35% by weight TS similarly to the way described in Example 1.

The remaining three days a week, both grain and pasture plants were added as follows: 300 ml digested sludge was removed from the reactor 402 and mixed for about 1 min with 25 g pasture plants, corresponding to 7 g of volatile solids, in a food processor. 3.3 g ground grain, corresponding to about 3 g of volatile solids, was mixed with 6 ml water to a mixture with a dry solids content of 35% by weight TS. This mixture of grain was added to the mixture of pasture plants in the food processor, after which the entire mixture was introduced into the reactor 402 through the glass feed-through 404. A certain amount of digested sludge, about 20 ml, was removed and rejected each day to keep the volume in the reactor constant. Calculated as an average during the entire experiment, thus 10 g of volatile solids was added per day, corresponding to 3.3 g of volatile solids per litre of reactor liquid and day, of which 7 g of volatile solids per day was grain and 3 g of volatile solids per day was pasture plants. The residence time in the reactor 402 was about 150 days.

Figure 8:
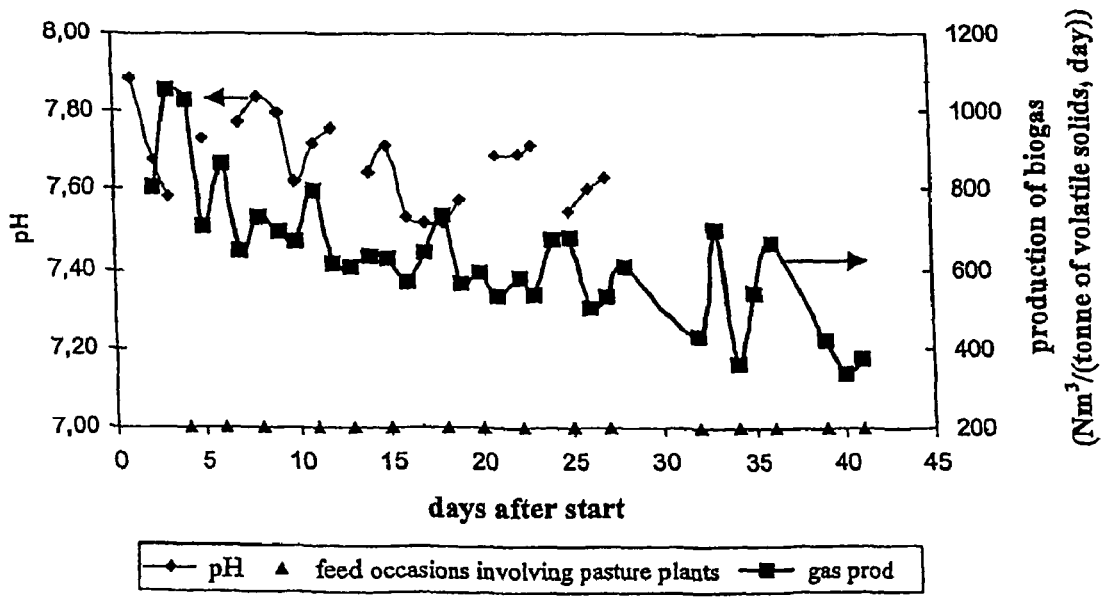
FIG. 8 shows the production of biogas per tonne of volatile solids and day in a second exemplary experiment.

FIG. 8 shows the production of biogas per day in the unit Nm³ of biogas per added tonne of volatile solids and day as a function of the number of days after start. As appears from FIG. 8, the system has still not after 40 days been stabilised. However, it may be read from FIG. 8 that the average production of biogas from day 32 to day 39 was about 561 Nm³ biogas per tonne of volatile solids and day. Calculated on the charged grain and pasture plants, the average production was 505 Nm³ of biogas per tonne of grain+pasture plants and day. Calculated on the dry solids content of the charged grain and pasture plants, the average production was 541 Nm³ biogas per tonne of dry solids and day. The produced biogas was collected at regular intervals and analysed with respect to methane content. At the end of the experiment, the methane content was 50-51%. FIG. 8 also shows the pH of the reactor liquid during the experiment. Except for certain disturbances, the pH was relatively stable in the range 7.5-7.8. The removed digested sludge had a dry solids content of 6.3% by weight TS and a volatile solids content of 83.9% by weight VS. The contents of volatile fatty acids were approximately the same as in Example 1, although stability had still not been achieved after 40 days.

As is evident from the results in Example 2, also such a moderate addition as 30% (calculated on the charged amount of volatile solids per day) of non-dried pasture plants strongly deteriorates the gas production in the reactor compared with the case involving digestion of grain only, like in Example 1. This may be caused by the fact that the removal of as much as 300 ml digested sludge to be mixed with pasture plants in the food processor had interfered with the process in the reactor.

Example 3

A device 400 of the type as described above was used for the experiment. At the start of the experiment, 3 l of digested sludge from the above-mentioned full-scale plant was charged. The origin of the digested sludge is thus apparent from the Table 1 above.

Each day, 10 g of pelletised grain offal was charged to the reactor 402. The grain offal essentially consisted of husks, stems and rejected grains. The grain offal had first been dried in an oven and then pelletised in a pelletising machine. The pellets were ground in the above-mentioned laboratory mill to a particle size of about 1 mm. The dry solids content of the ground pellets was 88.6% by weight TS and the volatile solids content was 96.5% by weight VS. Thus, each day 8.55 g of volatile solids was charged, corresponding to barely 3 g of volatile solids per litre of reactor liquid and day. The ground pellets were mixed with 18 ml of water to a substrate mixture with a dry solids content of 35% by weight TS and a volume of 25 ml. For practical reasons, it was necessary to dilute the substrate mixture to be able to introduce it into the tight glass feed-through 404 by means of a syringe. For this reason, 100 ml digested sludge per day was removed. 75 ml of this digested sludge was mixed with the substrate mixture and introduced together with the substrate mixture into the reactor 402. The remaining 25 ml of the digested sludge was rejected to keep the volume in the reactor 402 constant. The residence time in the reactor was 120 days with the above-described charging.

Figure 9:
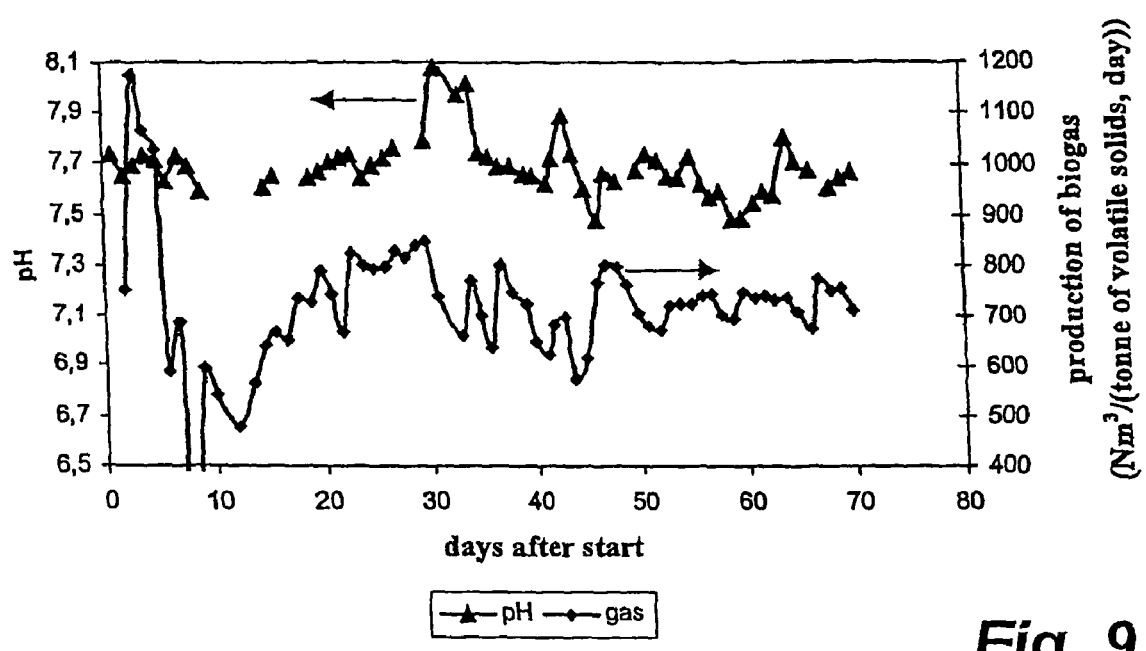
FIG. 9 shows the production of biogas per tonne of volatile solids and day in a third exemplary experiment.

FIG. 9 shows the production of biogas per day in the unit Nm³ of biogas per added tonne of volatile solids as a function of the number of days after start. As appears from FIG. 9, the production was first somewhat irregular. From day 50, the production became stable. As appears from FIG. 9, the average production of biogas is from day 50 to day 70 about 722 Nm³ of biogas per tonne of volatile solids and day. Calculated on the charged pellets, the average production was 616 Nm³ of biogas per tonne of pellets and day. Calculated on the dry solids content of charged pellets, the average production was 697 Nm³ of biogas per tonne of dry solids and day. The produced biogas was collected at regular intervals and analysed with respect to methane content. In stable gas production, the methane content was 51-53%. FIG. 9 also shows the pH of the reactor liquid during the experiment. Except for certain disturbances, the pH was relatively stable in the range 7.5-7.7. The removed digested sludge had a dry solids content of 6.8% by weight TS and a volatile solids content of 85.9% by weight VS. The contents of fatty acids were generally lower than in Example 1, which emphasises that the operation in the experiment was very stable.

Thus, it is evident from FIG. 9 that the production of biogas was essentially as great as in Example 1. In Table 2 below, the production of biogas in the three experiments has been compiled. As is evident, a considerably lower gas production was achieved in the experiment in Example 2, where pasture plants were added, than in the experiments in Examples 1 and 3.

TABLE 2

Compilation of the results of the experiments

| Example | Substrate | Biogas production Nm³ biogas/tonne of volatile solids and day |
|---|---|---|
| 1 | Grain | 700 |
| 2 | Grain + pasture plants | 561 |
| 3 | Pelletised grain offal | 722 |

It has been found in the experiments that the substrate mixtures prepared from ground grain and pelletised grain offal, respectively, and with a dry solids content of 35% by weight TS were definitely pumpable although they could not be injected into the glass reactor 402 by means of a syringe.

Pumpable substrate mixtures with a dry solids content of up to 42% by weight TS could be provided by means of ground grain.

The invention claimed is:

1. A method of producing biogas by anaerobic digestion of organic matter, comprising:
   drying organic matter to a dry solids content of at least 70% by weight total solids (TS) and subsequently pelletising the same,
   grinding and mixing the pelletised organic matter with a liquid to form a slurry, wherein the pelletized organic matter is ground such that at least 80% by weight of the organic matter obtains a particle size of 0.5-3 mm,
   contacting the slurry with biogas-producing bacteria for digestion under anaerobic conditions in a reactor, and digesting the slurry while producing biogas.

2. A method as claimed in claim 1, wherein the dried and pelletised matter is ground before being mixed with said liquid to form the slurry.

3. A method as claimed in claim 1, wherein an additional organic matter being a different type than the organic matter is also digested in the reactor, at least 10% by weight of the total dry solids introduced into the reactor originating from the dried and pelletised organic matter.

4. A method as claimed in claim 1, wherein the liquid with which the organic matter is mixed is essentially pure water.

5. A method as claimed in claim 1, wherein the liquid with which the organic matter is mixed at least partly is digested sludge which is removed from the reactor.

6. A method as claimed in claim 1, wherein the pelletised organic matter is mixed in a premixing tank with a liquid to form said slurry with a dry solids content of 15-45% by weight total solids (TS), and this slurry is then introduced into the reactor to be digested at a dry solids content of 5-10% by weight total solids (TS).

7. A method as claimed in claim 1, wherein the dried and pelletised organic matter is dried green matter, such as dried agricultural products.

8. A method as claimed in claim 1, wherein the organic matter is ground in a separate grinding process before being pelletised.

9. A method as claimed in claim 1, wherein the dried and pelletised matter is mixed with said liquid to form the slurry before being ground.

* * * * *